United States Patent [19]

Seppelt et al.

[11] Patent Number: 4,767,782
[45] Date of Patent: Aug. 30, 1988

[54] PROPARGYL CINNAMATES, THEIR PREPARATION AND THEIR USE FOR CONTROLLING PESTS

[75] Inventors: Wolfgang Seppelt, Bobenheim-Roxheim; Hans-Juergen Neubauer, Mannheim; Heinrich Adolphi, Limburgerhof; Peter Hofmeister, Neustadt, all of Fed. Rep. of Germany

[73] Assignee: BASF Aktiengesellschaft, Ludwigshafen, Fed. Rep. of Germany

[21] Appl. No.: 17,242

[22] Filed: Feb. 20, 1987

[30] Foreign Application Priority Data

Feb. 26, 1986 [DE] Fed. Rep. of Germany ....... 3606068

[51] Int. Cl.$^4$ ............................................ A01N 37/10
[52] U.S. Cl. ..................... 514/543; 560/104; 560/55; 560/75; 560/59; 549/447; 514/533
[58] Field of Search .............. 560/104, 55, 75, 59; 549/447; 514/543, 533

[56] References Cited

U.S. PATENT DOCUMENTS 3,975,429 8/1976 Henrick et al. ..................... 560/104
3,996,380 12/1976 Henrick ............................. 514/533
4,259,350 3/1981 Morisawa et al. ................. 514/533

FOREIGN PATENT DOCUMENTS 900554 7/1962 United Kingdom .

OTHER PUBLICATIONS

Klemm et al, J. Org. Chem., vol. 44, pp. 4524–4527 (1979).

Primary Examiner—James H. Reamer
Attorney, Agent, or Firm—Keil & Weinkauf

[57] ABSTRACT

Cinnamates of the formula I

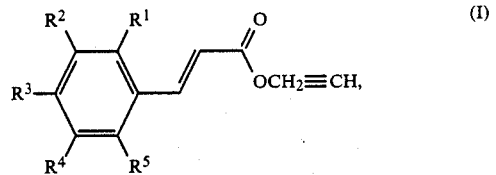

where $R^1$, $R^2$, $R^3$, $R^4$ and $R^5$ have the meanings stated in the description, processes for their preparation, and their use for pest control.

17 Claims, No Drawings

PROPARGYL CINNAMATES, THEIR PREPARATION AND THEIR USE FOR CONTROLLING PESTS

It has been disclosed that alkyl esters of alkynoic acids or alkynyl esters are useful for controlling mites (U.S. Pat. Nos. 4,024,278 and 3,996,380). However, the effect on arachnids is limited.

We have found that propargyl cinnamates of the formula I

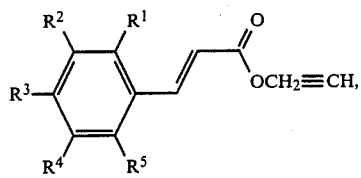

where $R^1$, $R^2$, $R^3$, $R^4$ and $R^5$ are identical or different and independently of one another are each H, F, Cl, Br, branched or straight-chain alkyl or alkenyl of not more than 4 carbon atoms, alkoxy or alkenyloxy of not more than 4 carbon atoms which may be substituted by halogen, and $R^2$ and $R^3$ together may form the moiety —O—CH$_2$—O—, or are each phenyl or phenoxy which may be substituted in the 3- and/or 4-position by halogen, alkyl or alkoxy of not more than 3 carbon atoms or by the moiety —O—CH$_2$—O—, possess very good insecticidal, acaricidal and in particular ovicidal or ovo-larvicidal activity and are superior to known active ingredients having a similar structure and the same direction of action.

The esters of the formula I can be obtained by reacting appropriate cinnamic acids (II) with propargyl alcohol (cf. Houben-Weyl, Methoden der organischen Chemie, volume VIII, page 516 et seq., Georg-Thieme Verlag, Stuttgart 1952).

The reaction can be carried out in a conventional manner by adding a catalyst, such as sulfuric acid, a halohydric acid, sulfonic acid or an acidic ion exchanger, and the equilibrium of the esterification can be shifted in the desired direction by removing the water or the ester I from the reaction mixture, for example by azeotropic distillation or by binding the water to sulfuric acid or hydrohalic acid.

It is also possible to react the corresponding acyl halide III, in which Hal(ogen) is fluorine, chlorine or bromine, with propargyl alcohol in the presence of an acid acceptor (Houben-Weyl, Methoden der organischen Chemie, volume VIII, page 543 et seq., Georg Thieme Verlag, Stuttgart 1952).

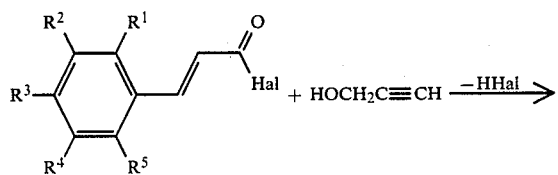

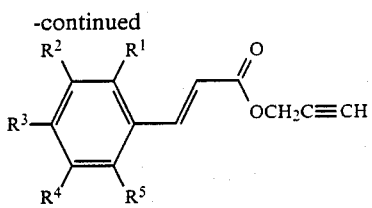

Suitable acid acceptors are the conventional basic agents, in particular aliphatic, aromatic and heterocyclic amines, eg. triethylamine, dimethylamine, piperidine, diazabicyclooctane, dimethylaniline, dimethylbenzylamine, pyridine, lutidine or dimethylaminopyridine. Alkali metal carbonates, such as sodium carbonate or potassium carbonate are also useful acid acceptors.

The reaction can be carried out in a solvent or diluent. Some of the stated acid acceptors themselves or, for example the following solvents or diluents or mixtures of these are suitable for this purpose: aliphatic and aromatic hydrocarbons and chlorohydrocarbons, such as petroleum ether, benzene, toluene, xylene, gasoline, dichloromethane, chloroform, tetrachloromethane, 1,2-dichloromethane or chlorobenzene, ethers, such as diethyl ether, di-n-butyl, ether, methyl tert-butyl ether, tetrahydrofuran or dioxane, ketones, eg. acetone, methyl ethyl ketone or methyl isopropyl ketone, and nitriles, such as acetonitrile or propionitrile.

The starting materials are usually used in a stoichiometric ratio. An excess of one or other of the starting materials may however be advantageous in specific cases.

The reaction usually takes place at an adequate rate at above 0° C. Since heat is generally evolved during the reaction, it may be advantageous to provide a means of cooling.

The novel propargyl cinnamates may furthermore be prepared by virtually any known method of ester synthesis, for example by reacting corresponding cinnamic anhydrides (cf. Houben-Weyl loc. cit., page 478) with propargyl alcohol, by reacting appropriate cinnamic acid salts with propargyl halides, by transesterification reactions (cf. Houben-Weyl, loc. cit., pages 508-628; C. Ferri, Reaktionen der organischen Synthese, page 446 et seq., Georg-Thieme Verlag, Stuttgart 1978 and S. Patai, The Chemistry of Carboxylic Acids and Esters, page 505 et seq., Interscience Publishers, London 1969), or, for example, from substituted aromatic aldehydes by condensation with suitably activated acetates (cf. J. Org. Chem. of USSR (1970), 2309).

The cinnamic acids required as starting materials are either known and in some cases commercially available, or they can be prepared by well known chemical methods (cf. Methodicum Chimicum, Georg Thieme Verlag, Stuttgart 1975, vol. 5, page 573 et seq or, for example, Organic Reactions, John Wiley and Sons, New York 1967, vol. 15, page 204 et seq.). Some of the cinnamoyl chlorides prepared have been obtained according to Houben-Weyl, loc. cit., page 463 et seq.

All novel compounds of the formula (I) can be prepared by appropriately modifying the Example below.

EXAMPLE 3.75 g of propargyl alcohol are added to 12.0 g of 2-methoxycinnamoyl chloride in 30 ml of tetrahydrofuran, and 20 ml of pyridine are added dropwise while cooling with ice. The mixture is stirred for 8 hours at room temperature, filtered and evaporated down under reduced pressure. The residue is taken up in 80 ml of ethyl acetate, the solution is washed twice with 10% strength HCl and twice with water and dried over Na$_2$SO$_4$, the solvent is stripped off under reduced pressure and the residue is purified by column chromatography (1:1 hexane/ethyl acetate). After removal of the mobile phase, 9.9 g of propargyl 2-methoxycinnamate remain as a white powder.

Mp. 86°–87° C.

Yield: 9.9 g (75% of theory)

Analysis: calculated C 72.2, H 5.6; found C 72.3, H 5.9.

$^1$H NMR (CDCl$_3$, 300 MHz): 803 d (1H); 7.50 d (1H); 7.35 t (1H); 6.90 m (2H); 6.58 d (1H); 4.80 sd (2H); 3.90 s (3H); 2.50 st (4H).

The active ingredients shown in the table below together with physical data (refractive index n$_D$ or mp. in °C.) were obtained from corresponding intermediates by appropriate modification of the above method; those compounds which are not further characterized can be obtained by one of the methods stated above. They are expected to have a similar biological action.

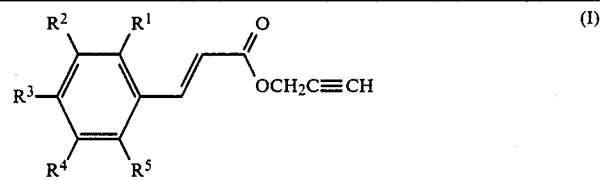

(I)

| Example No. | R$^1$ | R$^2$ | R$^3$ | R$^4$ | R$^5$ | n$_D$/mp. |
|---|---|---|---|---|---|---|
| 2 | F | H | H | H | H | 40° C. |
| 3 | Cl | H | H | H | H | 30° C. |
| 4 | H | Cl | H | H | H | 43–45° C. |
| 5 | H | H | CH$_3$ | H | H | 44–46° C. |
| 6 | H | H | i-C$_3$H$_7$ | H | H | $^{27}$1.5697 |
| 7 | H | H | OCF$_2$CF$_2$H | H | H | $^{25}$1.5121 |
| 8 | H | H | F | H | H | 32–34° C. |
| 9 | H | H | t-C$_4$H$_9$ | H | H | $^{21}$1.5618 |
| 10 | H | H | OCH$_3$ | H | H | 45–59° C. |
| 11 | H | OCH$_3$ | OCH$_3$ | OCH$_3$ | H | 93° C. |
| 12 | Cl | H | Cl | H | H | 92–95° C. |
| 13 | H | H | Cl | H | H | 56–58° C. |
| 14 | H | H | OC$_2$H$_5$ | H | H | 47–48° C. |
| 15 | H | H | C$_6$H$_5$ | H | H | 99–100° C. |
| 16 | H | —O—CH$_2$—O— | | H | H | 120–121° C. |
| 17 | Cl | Cl | Cl | H | H | 116° C. |
| 18 | H | Cl | H | Cl | H | 106° C. |
| 19 | H | H | —O–CH$_2$–CH=CH$_2$ | H | H | $^{24}$1.5986 |
| 20 | H | CH$_3$ | H | H | H | $^{21}$1.5735 |
| 21 | CH$_3$ | CH$_3$ | H | H | H | $^{21}$1.5740 |
| 22 | H | CH$_3$ | Br | H | H | 66–67° C. |
| 23 | OCH$_3$ | OCH$_3$ | H | H | H | 76–77° C. |
| 24 | H | OCH$_3$ | OCH$_3$ | H | H | 105–106° C. |
| 25 | Cl | H | H | H | Cl | 74–75° C. |
| 26 | OCH$_3$ | H | H | H | H | 86–87° C. |
| 27 | H | F | H | H | H | 31–32° C. |
| 28 | H | H | H | H | H | $^{22}$1.5849 |
| 29 | H | H | O—t-C$_4$H$_9$ | H | H | |
| 30 | H | Br | OCH$_3$ | H | H | 95° C. |
| 31 | H | H | OC$_6$H$_5$ | H | H | 45–47° C. |
| 32 | H | H | —O—C$_6$H$_4$—OCH$_3$ | H | H | 30–40° C. |
| 33 | H | H | 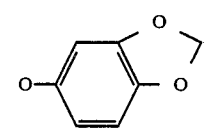 | H | H | 30° C. |
| 34 | H | H | —O—C$_6$H$_4$—Cl | H | H | 60–70° C. |

-continued

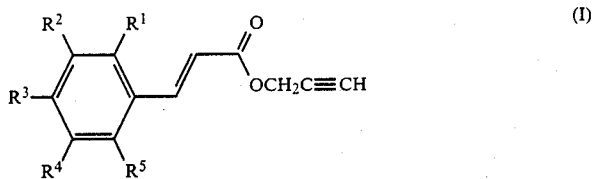

| Example No. | $R^1$ | $R^2$ | $R^3$ | $R^4$ | $R^5$ | $n_D$/mp. |
|---|---|---|---|---|---|---|
| 35 | H | H | 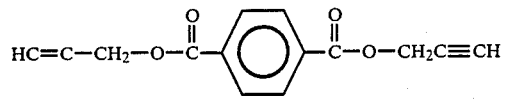 | H | H | 30° C. |

In the following examples of the biological action, the compound

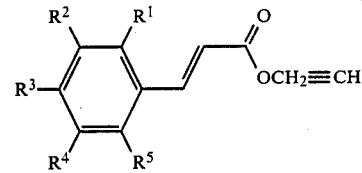

disclosed in U.S. Pat. No. 3,996,380 was chosen as a comparative agent.

Prodenia litura (cottonworm), action on egg deposits

The female moth lays its eggs in close groups on parchment paper. 2 days after the eggs have been laid, cut-out paper strips which carry about 200–300 eggs are dipped for about 5 seconds into the aqueous formulation of active ingredient (concentrated stated in g of active ingredient per 100 g of solution). Thereafter, they are placed in a Petri dish (10 cm diameter) on moist wadding.

Evaluation is carried out after the untreated control group has hatched, ie. after from 5 to 6 days.

Samples which are classified as effective are those where no hatching of caterpillars takes place. If isolated caterpillars appear, this is evaluated as the limit of activity.

| Example | | |
|---|---|---|
| 2 | 0.02% | about 80% mortality |
| 6 | 0.04% | about 80% mortality |
| 28 | 0.02% | 100% mortality |
| Comparative agent | 0.1% | about 45% mortality |

Dysdercus intermedius (cotton stainer), ovicidal action

Pieces of self-adhesive tape (about 0.8 cm) are stuck to the upper edge of push-in labels.

24 hours before the beginning of the experiment, the eggs collected in a vessel are attached to the edge of the self-adhesive tape by dipping the labels into the vessel.

The eggs are immersed in the aqueous formulation of active ingredient for about 5 seconds, and the labels are dripped onto filter paper. During this procedure, the eggs should not be placed on the paper.

The labels cut to size are placed in plastic pallets, the self-adhesive tape facing upward. A roll of cottonwool which is half-moistened with water is placed in the beaker in order to avoid drying-out, and the pallet is covered with a glass plate.

Rating is carried out after about 8 days (in the case of the control, the larvae must have hatched).

In this test, for example, the compounds 2, 5, 8, 13, 14, 21, 27 and 28 were superior to the comparative agent.

We claim:

1. A propargyl cinnamate of the formula (I)

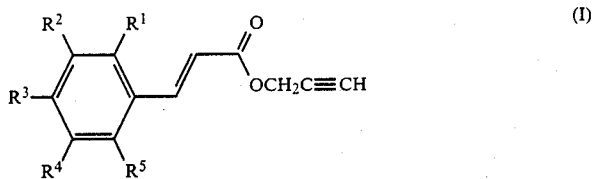

where $R^1$, $R^2$, $R^3$, $R^4$ and $R^5$ are identical or different and independently of one another are each H, F, Cl, Br, branched or straight-chain alkyl or alkenyl of not more than 4 carbon atoms, alkoxy or alkenyloxy of not more than 4 carbon atoms which may be substituted by halogen, and $R^2$ and $R^3$ together may form the moiety —O—CH$_2$—O—, or are each phenyl or phenoxy which may be substituted in the 3-position, 4-position or the 3- and 4-position by halogen, alkyl or alkoxy of not more than 3 carbon atoms or by the moiety —O—CH$_2$—O—, provided that when each of $R_1$, $R_2$, $R_3$, $R_4$ and $R_5$ are identical they are not H.

2. The propargyl cinnamate of claim 1 wherein $R^1$ is F and $R_2$, $R_3$, $R_4$ and $R_5$ are H.

3. The propargyl cinnamate of claim 1 wherein $R^2$ is F and $R^1$, $R^3$, $R^4$ and $R^5$ is H.

4. The propargyl cinnamate of claim 1 wherein $R^3$ is F and $R^1$, $R^2$, $R^4$ and $R^5$ are H.

5. The propargyl cinnamate of claim 1 wherein $R^3$ is —CH$_3$ and $R^1$, $R^2$, $R^4$ and $R^5$ are H.

6. The propargyl cinnamate of claim 1 wherein $R^3$ is Cl and $R^1$, $R^2$, $R^4$ and $R^5$ are H.

7. The propargyl cinnamate of claim 1 wherein $R^3$ is —OC$_2$H$_5$ and $R^1$, $R^2$, $R^4$ and $R^5$ are H.

8. The propargyl cinnamate of claim 1 wherein $R^1$ and $R^2$ are —CH$^3$ and $R^3$, $R^4$ and $R^5$ are H.

9. A pesticide comprising a solid or liquid carrier and an effective amount of one or more propargyl cinnamates of the formula I

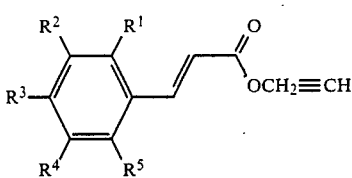

where $R^1$, $R^2$, $R^3$, $R^4$ and $R^5$ are identical or different and independently of one another are each H, F, Cl, Br, branched or straight-chain alkyl or alkenyl of not more than 4 carbon atoms, alkoxy or alkenyloxy of not more than 4 carbon atoms which may be substituted by halogen, and $R^2$ and $R^3$ together may form the moiety —O—CH$_2$—O—, or are each phenyl or phenoxy which may be substituted in the 3-position, 4-position or the 3- and 4-position by halogen, alkyl or alkoxy of not more than 3 carbon atoms or by the moiety —O—CH$_2$—O—.

10. The pesticide of claim 9 wherein $R^1$ is F and $R^2$, $R^3$, $R^4$ and $R^5$ is H.

11. The pesticide of claim 9 wherein $R^2$ is F and $R^1$, $R^3$, $R^4$ and $R^5$ is H.

12. The pesticide of claim 9 wherein $R^3$ is F and $R^1$, $R^2$, $R^4$ and $R^5$ are H.

13. The pesticide of claim 9 wherein $R^3$ is —CH$_3$ and $R^1$, $R^2$, $R^4$ and $R^5$ are H.

14. The pesticide of claim 9 wherein $R^3$ is Cl and $R^1$, $R^2$, $R^4$ and $R^5$ are H.

15. The pesticide of claim 9 wherein $R^3$ is —OC$_2$H$_5$ and $R^1$, $R^2$, $R_4$ and $R_5$ are H.

16. The pesticide of claim 9 wherein $R^1$ and $R^2$ are —CH$_3$ and $R^3$, $R^4$ and $R^5$ are H.

17. A method of controlling pests comprising applying an effective amount of one or more propargyl cinnamates of formula I

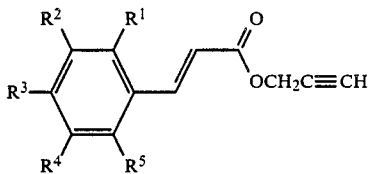

where $R^1$, $R^2$, $R^3$, $R^4$ and $R^5$ are identical or different and independently of one another are each H, F, Cl, Br, branched or straight-chain alkyl or alkenyl of not more than 4 carbon atoms, alkoxy or alkenyloxy of not more than 4 carbon atoms which may be substituted by halogen, and $R^2$ and $R^3$ together may form the moiety —O—CH$_2$—O—, or are each phenyl or phenoxy which may be substituted in the 3- and/or 4-position by halogen, alkyl or alkoxy of not more than 3 carbon atoms or by the moiety —O—CH$_2$—O— to pests or their habitat.

* * * * *

UNITED STATES PATENT AND TRADEMARK OFFICE
CERTIFICATE OF CORRECTION

PATENT NO. : 4,767,782

DATED : August 30, 1988

INVENTOR(S) : Seppelt et al.

It is certified that error appears in the above-identified patent and that said Letters Patent is hereby corrected as shown below:

Title page:

Foreign Application Priority Data Should be:

3606168 not (3606068)

Signed and Sealed this

Fourth Day of April, 1989

Attest:

Attesting Officer

DONALD J. QUIGG

Commissioner of Patents and Trademarks